US009161866B2

(12) United States Patent
Schmitz

(10) Patent No.: US 9,161,866 B2
(45) Date of Patent: Oct. 20, 2015

(54) ARTICLES WITH OVERFOLDED AND ATTACHED SIDE MARGINS

(75) Inventor: Christoph Schmitz, Euskirchen-Stotzheim (DE)

(73) Assignee: CONCEPTS FOR SUCCESS (C4S), Euskirchen-Stotzheim (DE)

( * ) Notice: Subject to any disclaimer, the term of this patent is extended or adjusted under 35 U.S.C. 154(b) by 398 days.

(21) Appl. No.: 13/511,902

(22) PCT Filed: Nov. 24, 2010

(86) PCT No.: PCT/EP2010/068158
§ 371 (c)(1),
(2), (4) Date: May 24, 2012

(87) PCT Pub. No.: WO2011/064272
PCT Pub. Date: Jun. 3, 2011

(65) Prior Publication Data
US 2012/0238985 A1    Sep. 20, 2012

(30) Foreign Application Priority Data

Nov. 24, 2009  (GB) .................................. 0920571.7
May 5, 2010   (GB) .................................. 1007486.2
Oct. 1, 2010   (GB) .................................. 1016544.7

(51) Int. Cl.
A61F 13/49   (2006.01)
A61F 13/495  (2006.01)
A61F 13/15   (2006.01)
A61F 13/496  (2006.01)

(52) U.S. Cl.
CPC ......... *A61F 13/495* (2013.01); *A61F 13/15593* (2013.01); *A61F 13/15804* (2013.01); *A61F 13/49* (2013.01); *A61F 13/496* (2013.01)

(58) Field of Classification Search
CPC ........... A61F 13/495; A61F 2013/4953; A61F 2013/4956; A61F 2013/51361
USPC ...................................................... 604/385.19
See application file for complete search history.

(56) References Cited

U.S. PATENT DOCUMENTS

| 3,426,756 A   | 2/1969 | Romanek |
| 3,885,568 A * | 5/1975 | Schaar ........................ 604/366 |
| 3,890,973 A * | 6/1975 | Davis et al. .................. 604/355 |
| 4,573,990 A   | 3/1986 | Ohsaki |

(Continued)

FOREIGN PATENT DOCUMENTS

| AU | 2005232329 | 5/2006 |
| EP | 1040800    | 10/2000 |

(Continued)

OTHER PUBLICATIONS

International Search Report for PCT/EP2010/068158, Completed by the European Patent Office on May 13, 2011, 4 Pages.

(Continued)

*Primary Examiner* — Lynne Anderson
*Assistant Examiner* — Kathryn E Ditmer
(74) *Attorney, Agent, or Firm* — Brooks Kushman P.C.

(57) ABSTRACT

The present invention is an article such as an article to be worn on the lower torso of a wearer, such as pants or diapers. The article has a flexible faeces separation member, such as a faeces trap sheet, which is attached in a particular way such that an effective separation of faeces from skin respectively genitals can be achieved.

19 Claims, 6 Drawing Sheets

(56) References Cited

U.S. PATENT DOCUMENTS

| | | | |
|---|---|---|---|
| 4,601,868 | A | 7/1986 | Radel et al. |
| 4,690,681 | A | 9/1987 | Haunschild et al. |
| 4,880,417 | A * | 11/1989 | Yabrov et al. ............... 604/355 |
| 4,883,481 | A | 11/1989 | Blanchard |
| 4,940,464 | A | 7/1990 | Van Gompel et al. |
| 5,147,345 | A | 9/1992 | Young et al. |
| 5,260,345 | A | 11/1993 | DesMarais et al. |
| 5,269,775 | A | 12/1993 | Freeland et al. |
| 5,462,541 | A | 10/1995 | Bruemmer et al. |
| 5,531,728 | A | 7/1996 | Lash |
| 5,714,156 | A | 2/1998 | Schmidt et al. |
| 5,800,416 | A | 9/1998 | Seger et al. |
| 5,897,544 | A * | 4/1999 | Ronnberg ............... 604/385.19 |
| 5,904,674 | A | 5/1999 | Bonjour |
| 6,010,490 | A * | 1/2000 | Freeland et al. ......... 604/385.19 |
| 6,132,409 | A * | 10/2000 | Vogt et al. ................... 604/348 |
| 6,186,992 | B1 | 2/2001 | Roe et al. |
| 6,315,764 | B1 | 11/2001 | Faulks et al. |
| 6,372,953 | B1 | 4/2002 | Young et al. |
| 6,406,464 | B1 * | 6/2002 | Palumbo et al. ............... 604/355 |
| 6,458,114 | B1 | 10/2002 | Mishima et al. |
| 7,153,295 | B2 | 12/2006 | Nakajima et al. |
| 7,238,175 | B2 | 7/2007 | Onishi et al. |
| 8,221,380 | B2 | 7/2012 | Schmitz |
| 2003/0120254 | A1 | 6/2003 | Franke et al. |
| 2004/0010842 | A1 | 1/2004 | Walsh |
| 2005/0148977 | A1 | 7/2005 | Van Gompel et al. |
| 2005/0203477 | A1 * | 9/2005 | Mishima et al. ......... 604/385.28 |
| 2006/0024744 | A1 * | 2/2006 | Mills et al. ..................... 435/7.1 |
| 2006/0025744 | A1 * | 2/2006 | Mishima et al. ....... 604/385.101 |
| 2006/0229582 | A1 | 10/2006 | LaVon |
| 2007/0088304 | A1 | 4/2007 | Sakano et al. |
| 2008/0172020 | A1 | 7/2008 | Schmitz |
| 2009/0018519 | A1 * | 1/2009 | Yoshida ................... 604/385.19 |
| 2009/0124991 | A1 | 5/2009 | Tsang et al. |
| 2010/0022982 | A1 | 1/2010 | Tonino |
| 2010/0094236 | A1 | 4/2010 | Schmitz |
| 2010/0121294 | A1 | 5/2010 | Okawa et al. |
| 2010/0324514 | A1 | 12/2010 | Minato et al. |
| 2012/0042493 | A1 | 2/2012 | Schmitz |

FOREIGN PATENT DOCUMENTS

| | | |
|---|---|---|
| EP | 1080707 | 3/2001 |
| EP | 1234563 | 8/2002 |
| EP | 1279388 | 1/2003 |
| EP | 1421926 | 5/2004 |
| EP | 2025311 | 2/2009 |
| EP | 2111832 | 10/2009 |
| EP | 2184043 | 5/2010 |
| GB | 2296660 | 7/1996 |
| JP | 08196565 | 8/1996 |
| JP | 8215228 | 8/1996 |
| WO | 9622755 | 8/1996 |
| WO | 9722319 | 6/1997 |
| WO | 0000111 | 1/2000 |
| WO | 0106974 | 2/2001 |
| WO | 0205603 | 1/2002 |
| WO | 03082168 | 10/2003 |
| WO | 2006102974 | 10/2006 |
| WO | 2006108029 | 10/2006 |
| WO | 2008037281 | 4/2008 |
| WO | 2008138018 | 11/2008 |
| WO | 2008141756 | 11/2008 |
| WO | 2009119376 | 10/2009 |
| WO | 2010057543 | 5/2010 |

OTHER PUBLICATIONS

Search Report for GB 0920571.7, Date of Search Mar. 18, 2010, 1 Page.

Search Report for GB 1016544.7, Date of Search Feb. 1, 2011, 1 Page.

Search Report for GB 1007486.2, Date of Search Sep. 3, 2010, 1 Page.

* cited by examiner

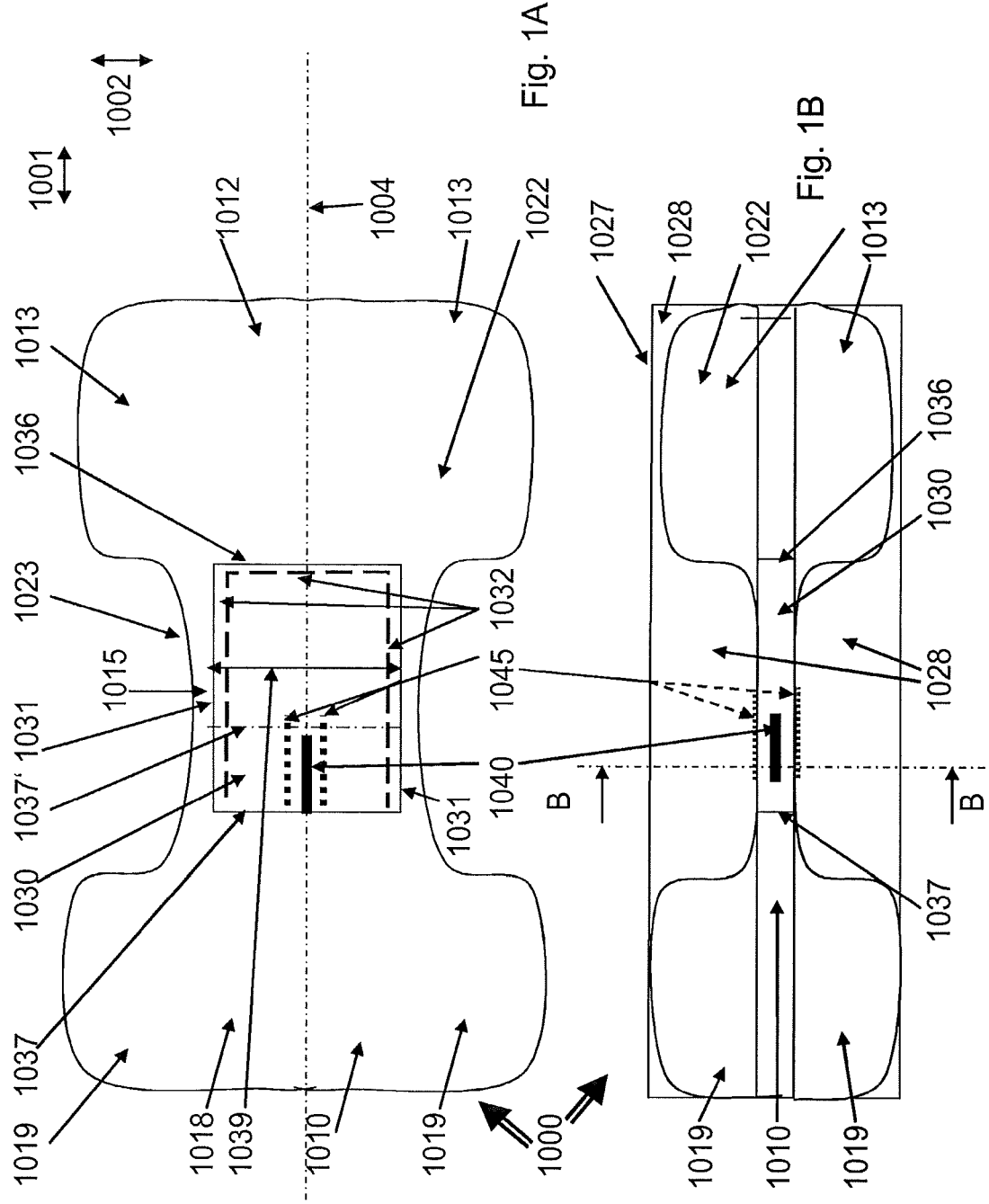

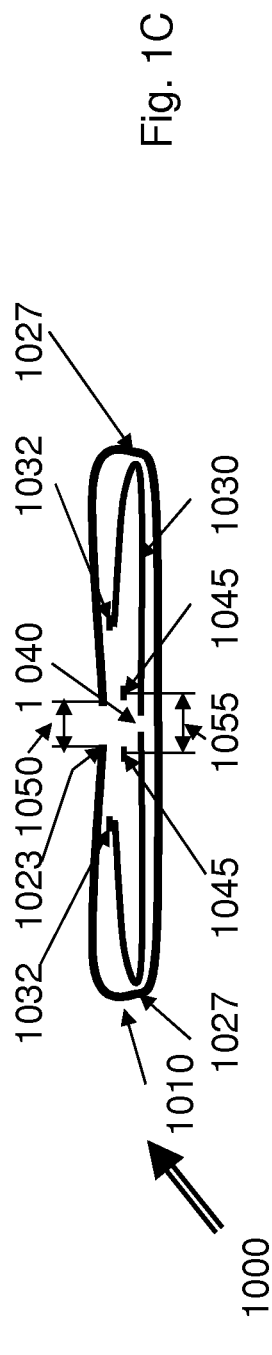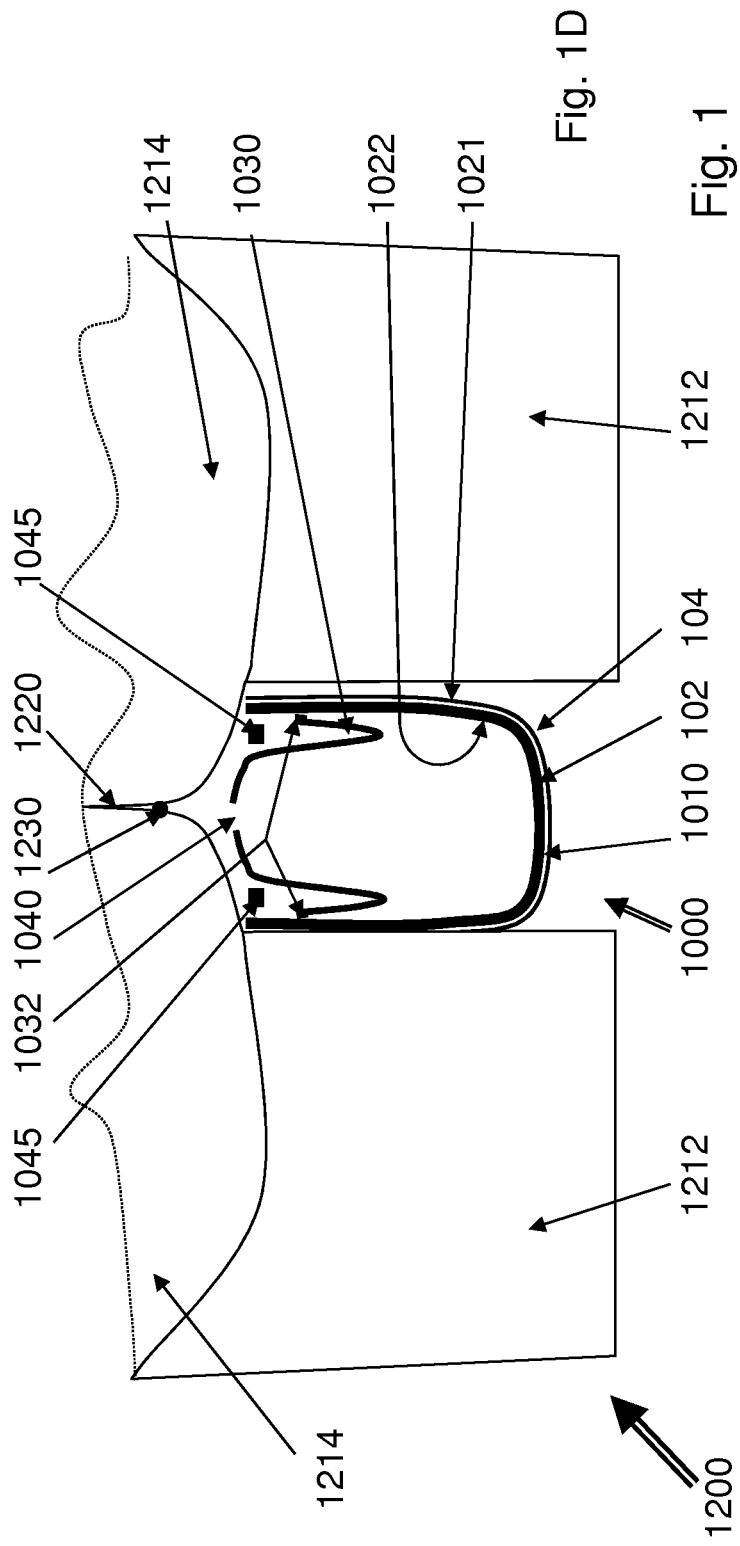

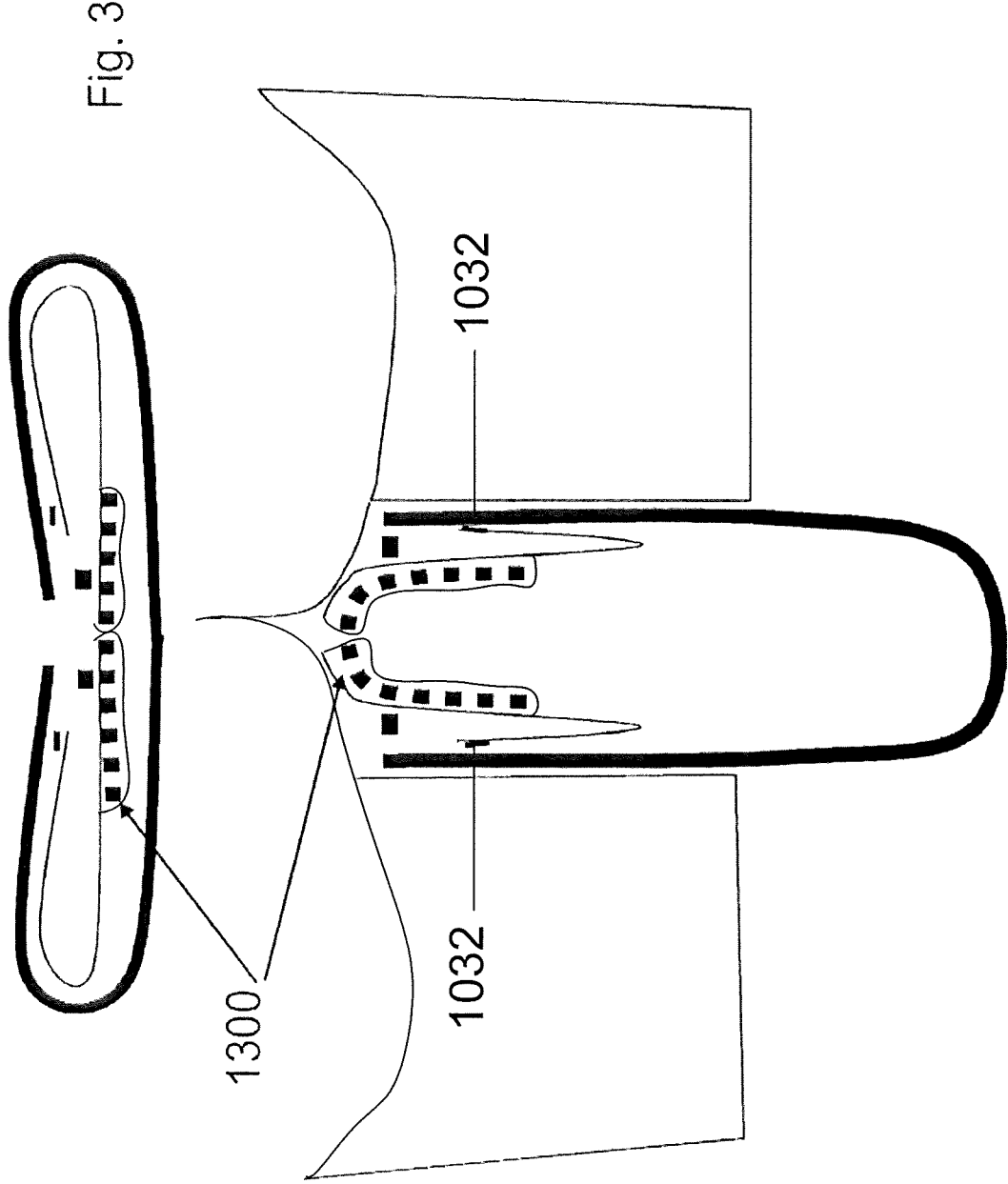

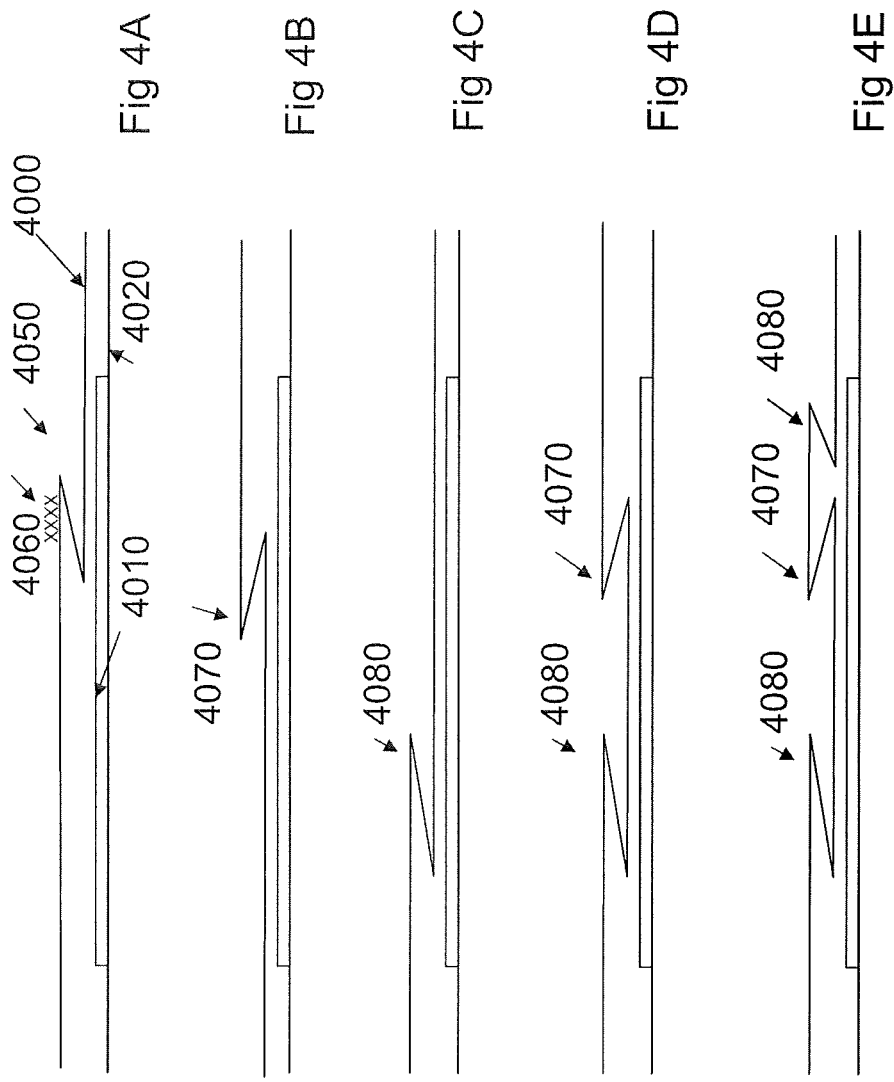

ARTICLES WITH OVERFOLDED AND ATTACHED SIDE MARGINS

CROSS-REFERENCE TO RELATED APPLICATION

This application is the U.S. national phase of PCT Appln. No. PCT/EP2010/068158 filed on Nov. 24, 2010, which claims priority to GB Patent Application No. 0920571.7 filed on Nov. 24, 2009, GB Patent Application No. 1007486.2 filed on May 5, 2010 and GB Patent Application No. 1016544.7 filed on Oct. 1, 2010 the disclosures of which are incorporated in their entirety by reference herein.

FIELD OF THE INVENTION

The present invention is an article such as a garment to be worn on the lower torso of a wearer, such as pants or diapers. The article is designed to provide good fit and allows to readily introduce elements for improving skin cleanliness of the wearer.

BACKGROUND

Articles, which are to be worn on the lower torso of a wearer such as pants or diapers, are constantly sought to be improved with regard to their fit on the wearer. Since several years, the focus has been put on doing so by improving the elasticity of the materials employed therein. In a recent approach, leg hoops have been introduced so as to provide sustained body conforming fit, such as described in WO06/102974A1 (C4S). Whilst these designs as well as their manufacturing (such as described in WO08/141756 or WO2010/057543) is quite simple, there is a need for even simpler designs.

In addition to simple and yet well fitting designs, the soiling of the wearer's skin by inadequate handling of faecal exudates in articles such as disposable absorbent articles and the like has long been identified as an issue, but although there has been proposed a plethora of solutions, there is at present no broad scale and functioning execution in the market.

In addition to the above mentioned patent publications, a further exemplary approach is disclosed in U.S. Pat. No. 5,269,775 (P&G) showing a topsheet for use in a disposable absorbent article which is divided into three trisections with different elastic properties. The topsheet may further have an aperture for communicating faecal material through the topsheet into a void space in the disposable absorbent article.

EP1279388A1 (P&G) describes absorbent articles, wherein cuffs are designed to provide a barrier function such as for faeces which is less sensitive to sagging upon loading.

U.S. Pat. No. 5,462,541 (K-C) describes an absorbent article comprising a topsheet, a backsheet, an absorbent core, and an elevating device for spacing the topsheet above the absorbent core to form a pocket-30 like shape. The topsheet can have an opening and the absorbent can have a hole therein, both of which receive and isolate waste material from the wearer.

WO 09/119376A1 (Uni-Charm) discloses a diaper with a spacer and a separator aiming at reducing the contamination of the skin in the external genital and perineal area by excretion. WO08/138018A1 (DSG) discloses an article having an absorbent core, a liquid pervious top sheet 35 and a liquid impervious backsheet. A pair of flexible elastic leg wraps extends outwardly from and alongside edges of the core, and includes a set of spaced-apart elastic strands. The leg wraps and the core form a reservoir for capturing bodily exudates. A set of fluid dams is defined by the strands during use of the article with each fluid dam capturing volume of liquid waste from passing between the leg wraps and a wearer.

The general principle of all these approaches is to provide a separation material for separating the faeces, once deposited, as much as possible from the skin of the wearer and/or from the genitals. To this end, the separation material is intended to be positioned in proximity of the anus of the wearer, be it in the form of the secondary topsheet, or of a separation barrier and so forth. However, it is believed that the key reason for the lack of market introduction of functioning products is that this registry between the faeces separation means and the anus is too often not maintained during use.

As long as this registry is intact, the separation may function, if there is a mis-alignment this might actually induce much more severe skin soiling, if not leakage incident, than without such a separation means. It is also believed that articles with such conventional faeces separation features may be more difficult to apply.

A first solution to this problem is described in co-pending patent application in the name of the present applicant Concepts for Success (Appl.-number GB-1004733, unpublished). Therein, the registry of anus and separation means, such as in the form of a secondary topsheet is achieved by affixing the product by means of leg hoops around the legs of the wearer.

However, there is still a need for a solution, which is not relying on the additional features of leg hoops, but thus provides faeces separation and ease of application by very simple means.

SUMMARY

The present invention is an article for being worn on the lower torso of a wearer, which comprises a basis which comprises a front region, a rear region and a crotch region there between, thereby defining a longitudinal (x-) and width (y-) direction, a longitudinal centreline and two opposite longitudinally extending side margins. The basis exhibits a first surface, intended to be oriented towards a wearer during use and a second opposite surface. The article further comprises a flexible faeces separation member, which is attached to the first surface of the basis, whereby the attachment is adapted to allow spacing apart of the flexible faeces separation member from the first surface of the basis at least along a portion of the longitudinal centreline.

The longitudinal side margins of the basis are overfolded such that they overlay the flexible faeces separation member at least in the crotch region and the overfolded longitudinal side margins are connected to the flexible faeces separation member by at least one pick-up connection per side, which (i) is positioned cross-directionally relative to the longitudinal centre line at a distance of less than 10 cm, preferably less than 5 cm, more preferably less than 2.5 cm thereto, and (ii) is positioned longitudinally at least in the crotch region of the article. The cross-directional distance of the pick-up connection to the longitudinal side margin may be less than 10 cm, preferably less than 5 cm, more preferably less than 2.5 cm. The pick up connection (iii) has a longitudinal extension of less than 30 cm, preferably less than 5 cm.

The article may comprise a stiffening element attached to the faeces trap sheet in the crotch region and to a leg hoop or the pick-up connection. The stiffening member may comprise a cross-directionally extending strip of material, having a stiffness higher than the stiffness of the flexible faeces separation member. Alternatively, the stiffening element may be formed by a cross directionally extending edge of the core.

Optionally, in the article according to the present invention the flexible faeces separation member may form a genital pocket.

The flexible faeces separation member may comprise faeces guide means for directional faeces transport, which may comprise surface property modifier preferably selected from the group consisting of
 a surface friction reducer,
 a surface wettability reducer,
 a faeces adherence reducer, and
 a surface structuring.

The surface structuring may comprise at least one cross-directionally extending faeces strip, connected with its rearward oriented margin to the basis or the flexible faeces separation member and exhibiting a first faeces strip surface oriented to the surface, to which it is connected, whilst its forward oriented margin is essentially unconnected.

The first faeces strip surface may different friction properties than the opposite surface, whereby the differences may be based on one or more of the following effects: (a) for essentially same surface materials by roughening, or additive treatment, and/or by using an aperture film material forming "formed film", and/or (b) for different surface materials the use of rough vs. smooth materials, and/or non-absorbent vs. absorbent materials.

The article may further comprise a flatulus filter material, optionally positioned in the waist hoop region or between the topsheet and the second opposite surface of the basis. The article may comprise a body adhering substance.

In one execution, the flexible faeces separation member is a faeces trap sheet, forming a faeces trap between the faeces trap sheet, which is overlying the first surface of the basis at least in the crotch region, and the first surface of the basis. The faeces trap may further comprise a faeces passage delimited at least partially by a discontinuity of the faeces trap sheet, and the passage can be adapted to allow faeces to be deposited between the faeces trap sheet and the first surface of the basis. The passage is preferably positioned along or intersecting the longitudinal centre line.

The discontinuity may be a slit extending through the faeces trap sheet, preferably extending essentially longitudinally, preferably at a length of at least 1 cm, preferably of a length less than 90% of the length of the faeces trap sheet. The discontinuity may intersect a margin of the-faeces trap sheet.

Alternatively, the discontinuity is formed by a cross-directionally extending fold- or bond line. then a portion of the faeces trap sheet may be in a double layer configuration adapted to form the genital pocket.

The flexible faeces separation member may have absorbent material connected thereto or which is integral therewith, such that the composite exhibits a teabag centrifuge absorbent capacity of at least 2 g/g. Preferably, the absorbent material is essentially unattached to the basis at least along the longitudinal centre line at least in a portion of the crotch region.

In another execution, the basis of the article comprises a first topsheet on its first surface adapted to form the flexible faeces separation member by one or more essentially cross-directionally extending forward (and/or backward) z-fold(s) in the first topsheet, whereby (i) the wearer oriented part of the forward z-fold is essentially unattached to the basis but attached by the pickup connection, and (ii) the base of the z-fold is attached to the basis at least in the proximity of the side margins of the basis. This z-fold may selected from the group of (a) a single z-fold, positioned forward of the anus and having the base, which is oriented towards the basis of the article connected thereto, and having the cross-bar running forwardly, such that a genital pocket is formed; and (b) a single z-fold positioned forward of the anus and having the base, which is oriented towards the basis of the article connected thereto and having the cross-bar running rearwardly, such that a faeces trap is formed; and (c) a dual z-fold comprising one of the z-folds according to (a) or (b), and a further z-fold positioned rearwardly of the anus having the base, which is oriented towards the basis of the article connected thereto, and having the cross-bar running forwardly, such that a faeces trap is formed. In this execution, the flexible faeces separation member may further comprise discontinuities, preferably apertures to allow faecal material to pass through.

BRIEF DESCRIPTION OF THE FIGURES

FIG. 1 A to D show schematically an article according to the present invention comprising a faeces trap sheet as a particular embodiment;

FIG. 3 depicts an article according to the present invention, further comprising a stiffening member.

FIG. 4 depicts embodiments according to the present invention comprising a flexible faeces separation member executed with cross-directional folds.

The same numerals across different figures denote identical features.

DETAILED DESCRIPTION

Figures 2A, 2B:
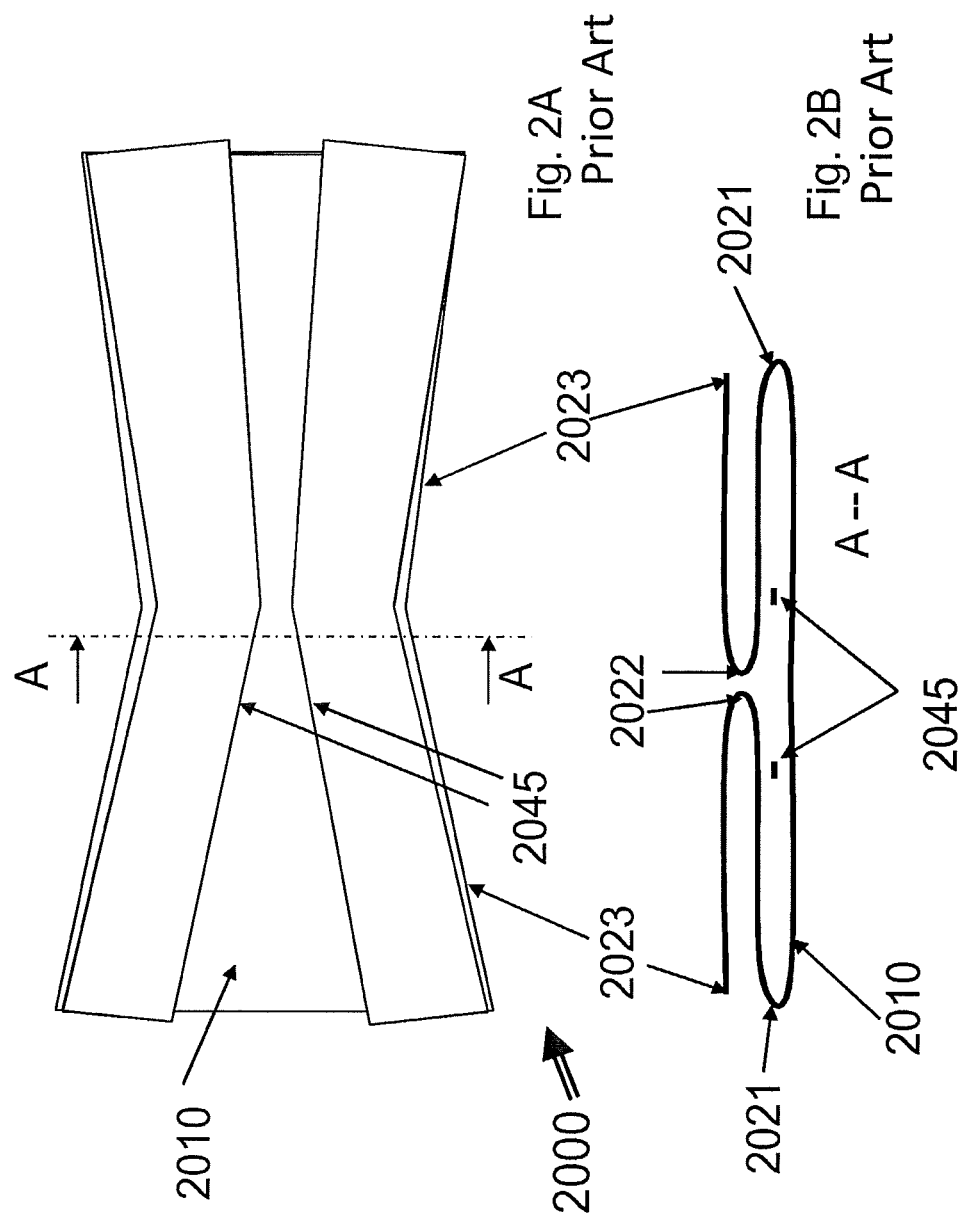
FIG. 2 depicts schematically prior art article designs.

The present invention relates to articles, typically worn by humans on the lower torso, i.e. pants style articles. The articles according to the present invention are adapted to provide improved fit and skin cleanliness by an improved functionality with regard to the handling of faeces as may be discharged thereto.

The articles according to the present invention comprise a centre piece comprising a front and a rear region, typically corresponding to the front and back waist regions of a wearer, and a crotch region there between, thereby defining the longitudinal orientation or x-direction of the article. The crotch region of the article corresponds to the crotch region of the wearer, which may be considered to terminate rearwardly beyond the anus and forwardly beyond the genitals, The article further may comprise side panel regions, which extend laterally outwardly of the centre piece along the width y-direction of the article at least in the front and/or rear waist region. Within the present context, this refers to an article in its in-use configuration. During manufacturing, or in a folded article after manufacturing respectively in the pre-use configuration, the side panels may be folded so as to overly the centre region, but are nonetheless considered as "extending laterally outwardly". The article according to the present invention is essentially symmetrical to its longitudinal centreline.

The present invention relates to articles which may be closed pants or pants-style articles or to articles, which are open products and which may be brought into a closed pants-style form upon donning such as conventional taped diapers. The present invention further relates to pre-forms of such articles, which may require addition of certain elements or performance of certain process steps to be functional as an article.

The articles according to the present invention comprise a basis, which may comprise well known elements of hygiene articles, such as an absorbent core, optionally with superabsorbent material and/or liquid distribution layers and a backsheet. In addition, the articles comprise a flexible faeces separation member, positioned on the surface of the basis which is intended to be oriented towards 30 the wearer during use. The flexible faeces separation member will be positioned at least in a portion of the article which is positioned in the crotch region of the article forwardly of the anus, when the article is worn. The flexible faeces separation member may be executed to be integral with the wearer oriented topsheet web of the article, or it may overlie a separate topsheet. A secondary absorbent core may be attached at least to a portion of the flexible faeces separation member. As will be discussed herein below, the faeces separation member can be positioned flat or in a folded position on the wearer oriented surface of the basis, but it is essential that it is sufficiently flexible—with regard to its properties but also with regard to its fixation to the base—to allow it to be spaced apart from this surface during the use at least along a portion of the longitudinally extending centre line of the article. This spacing is achieved by overfolding of the longitudinally extending side margins of the article respectively its pre-form towards the longitudinally extending centre-line at least in the crotch region of the article. Preferably, the overfolded side margins have a distance to the longitudinally extending centre line of less than 10 cm, preferably less than 5 cm or even less than 2.5 cm. Further, the overfolded side margins are connected to the flexible separation member at least in the crotch region by a pick-up connection, such as a glue region, line or even only a glue spot. This pick-up connection is positioned cross-directionally at a distance of less than 30 cm, preferably less than 10 cm or even less than 5 cm or even less than 2.5 cm from the longitudinal centre line. The pick-up connection is also positioned cross-directionally at a distance of less than 30 cm, preferably less than 10 cm or even less than 5 cm or even less than 2.5 cm from the longitudinal side margins of the centre piece. Preferably, the glue connection has a longitudinal extension of less than 30 cm, preferably less than 15 cm or even 15 less than 5 cm.

The principles of the present invention are now further explained by referring to FIG. 1, schematically showing one particular embodiment, the details of which will be described further herein below. FIG. 1 depicts a pre-form of an article in a state prior to longitudinally folding and applying the pick-up connection, as described herein below and depicted in FIG. 1B to D. As shown in FIG. 1 A, the flat out stretched pre-form of an article 1000 has a front waist region 1012 and a rear waist region 1018 connected by a crotch region 1015, thereby defining a longitudinal (x-) direction 1001 of the article. A width (y-) direction 1002 of the article corresponds to the right-left orientation on a wearer. Typically, the article is symmetrical to its longitudinal centreline 1004. Typically, the thickness (z-direction) of the article is much smaller than the length and width, and extends perpendicularly thereto.

In an in-use configuration, the respective front and rear regions are respectively connected so as to form a pants style product. This connecting can be done permanently such as typically applied in so called training pants. This connecting can be done by the user or his/her caretaker, such as typically applied in openable diapers. This connecting may also be a combination of any conventional closure means, including separately applied belts or hoops. The articles may be narrower in the crotch region than in the front or rear regions. As shown in FIG. 1A, front (1013) and rear (1019) side panels extend laterally outwardly of the centre piece in the front and rear regions. It should however be noted, that the present invention is evenly applicable, if the lateral extension of the side panels is less pronounced, including for example rectangularly shaped products which may be held in place by fixation means such as e.g. a belt.

Articles according to the present invention may have absorbent elements, as is the case for disposable absorbent articles such as baby or adult incontinence diapers, or for training pants and the like. Such articles may also be designed without integral absorbent elements, but may be combined with separate absorbent elements, such as when pants are used in combination with absorbent pads for the use in the context of adult incontinence or for feminine hygiene. Such articles may also be designed with no or relatively little absorbency, and may be used as disposable, or limited re-use underwear. Articles having no or only little absorbent capacity may be designed to withstand at least a limited amount of wash cycles without disintegrating.

Within the present context, the backsheet and core, and optionally other elements as commonly used in conventional articles, such as topsheets, are considered to form the basis of an article according to the present invention, denoted 1010 in the Figures. For example, the basis 1010 may include a core 102 and a backsheet 104. The core 102 may define a topsheet side 1022 and the backsheet 104 may define an outer surface 1021.

Within the context of the present invention, the pre-form of an article or the article itself comprises a basis, which may comprise the elements as described above. The articles or the basis of articles according to the invention exhibit a first, wearer oriented, or inner surface, often also referred to as the topsheet side 1022, and a second, opposite or outer surface 1028, often referred to as backsheet side. The topsheet oriented side is typically made of liquid pervious material so as to allow urine to penetrate through to the absorbent elements. The outer surface is typically made of liquid impervious materials, such as polymeric films or liquid impervious webs, all well known to a skilled person. Optionally, and often preferably, the outer material is at least in certain regions breathable, as may be achieved by using so called microporous films or the like.

When referring to the topsheet side as wearer oriented or inner surface of the article, it should be noted, that not all of this surface needs to be arranged so as to be in contact with the skin of the wearer, but parts may be folded away, or may be overlaid by other materials, as will also be discussed herein below. Similarly, not all of the backsheet or outer surface needs to be arranged away from the skin of a wearer, although any backsheet material which possibly may contact the skin of a wearer should be adapted with regard to skin friendliness.

Articles according to the present invention further comprise a layer 1030 overlying the user oriented surface 1022 of the basis, hereinafter referred to as "flexible faeces separation member". The flexible faeces separation member can be executed as two preferred embodiments, which are described in more detail herein below. In a first embodiment, which is depicted in FIG. 1, the flexible faeces separation member is executed as an additional web, hereinafter referred to as faeces trap sheet, which—together with the basis over which it is positioned and from which it may be spaced apart—forms a faeces trap. In a second embodiment, the flexible faeces separation member is integral with the cover of the basis, such as may be a conventional topsheet adapted to be flexibly spaced apart from the remainder of the basis in at least certain parts of the crotch region, such as by including a cross-directional fold.

A suitable material for the flexible faeces separation member is a soft web material, which should not cause skin irritation. This web may be designed to not allow faeces to penetrate through, although it may be designed so as to have a certain liquid permeability, optionally varying over the surface. Without intending any limitation, a material suitable for certain embodiments may be a non-woven material of a basis weight of about 15 to 30 g/m2, such as being made from PP-fibres having a thickness of from 0.1 dTex to 3 dTex or more. Such materials may also be composite materials, such as well known "SMS" composites, i.e. made of a layer of meltblown fibres sandwiched between two layers of spundbonded material. The flexible faeces separation member may have particular masking properties such as described in U.S. Pat. No. 5,462,541.

In a particular execution of the present invention, the flexible faeces separation member may have elastic properties, so as to enhance the contact to wearer's skin during use. Such as by attaching longitudinally extending elastic outwardly adjacent to the slit or opening of the flexible faeces separation member. Alternatively, the flexible faeces separation member may be executed as a web with elastic properties, optionally varying along or across the web.

The present invention further includes a particular attachment of the flexible faeces separation member by a pick-up connection. To this end, the longitudinal side margins of the basis are folded over so as to overlay the flexible faeces separation member at least in the crotch region, such that the longitudinal side margins are positioned at a cross-directional distance to the longitudinal centreline of less than 10 cm, preferably less than 5 cm, more preferably less than 2.5 cm. The pick-up connection of the overfolded side margins and the flexible faeces separation member is positioned cross-directionally close to the side margins, i.e. at a distance of less than 5 cm, preferably less than 5 mm, and not too far from the longitudinal centreline, i.e. at a distance of less than 10 cm, preferably less than 5 cm, more preferably less than 2.5 cm. The pick-up connection should not have a too long longitudinal extension as it might otherwise affect the overall fit of the article negatively, and thus the longitudinal extension should be less than 30 cm, preferably less than 15 cm, more preferably less than 5 cm. The pick-up connection may be made of a continuous connecting line or region or of one or more lines, regions or dots.

The flexible faeces separation member remains essentially unattached to the underlying basis at least in the proximity of the pick-up connection, such that upon donning and adapting the article to its in-use configuration, the pick-up connection will lift up the faeces trap sheet.

In particular embodiments, the articles of the present invention further comprise a stiffening member for supporting the spacing apart of the flexible faeces separation member from the basis. Such a stiffening member may be any stiff material exhibiting a stiffness higher than the flexible faeces separation member, e.g. when assessed according to the Taber stiffness test. Preferably, the stiffness is sufficient to urge the flexible faeces separation member towards the skin of the user. Such a stiffening member may be executed as one or more strips extending essentially cross-directionally and/or in the longitudinal direction of the article, and being affixed to the flexible faeces separation member at least in the proximity of the pick-up connection. As indicated in FIG. 3, which depicts an article in a position similar to the one shown in FIG. 1D, such a stiffening member 1300 is placed cross-directionally symmetrically to the longitudinal centre line laterally outwardly, either as a single piece, or as at least one piece per side located with its inner margin close to the product centreline and/or the inner margin of the opening for receiving the faeces. Preferably, the stiffening member does not extend into regions, where the flexible faeces separation member is connected to the basis. Preferably, the stiffening member strip has a longitudinal extension in the article of more than about 1 mm, preferably more than about 1 cm. It may have a rectangular shape, though other shapes—including shapes having in certain parts a significantly longer extension in the longitudinal direction of the article or closed structures like ovals or rings—are included in the present scope of the invention. Where appropriate, the stiffening member is preferably adapted to not obstruct passage of faeces through passages or apertures.

In a preferred execution of the present invention the flexible faeces separation member may be connected to a secondary absorbent core. In this execution, a primary absorbent core is essentially attached to the backsheet of the basis, as described already hereinabove. A secondary core is attached to the flexible faeces separation member at least in an area adjacent to the periphery of the discontinuity, and may function as a stiffener. In one variant, the secondary core is positioned forwardly of the discontinuity and may extend into the front region of the article. Such an embodiment provides particular advantages for the handling of faeces, as the secondary core may serve to effectively separate the genitals and the skin form the faeces. In another variant, the secondary core is positioned rearwardly, thusly providing particular benefits for a person in a supine position with urinary incontinence.

The primary and secondary core may—when seen in a longitudinal projection—be arranged in a "flushed" position, i.e. there is no overlap when projecting the extension onto the backsheet. Alternatively, there is an overlap in the projection onto the backsheet, which may be between 0 and 20 cm.

The secondary core may be essentially the same type as the primary one, and in a particular execution they may be cut off the same roll of roll stock, such as an aMaid material. For such an execution, both core pieces may be positioned on a continuous carrier web, which may 30 simultaneously function as the topsheet and even as flexible faeces separation member. As described in more detail in copending PCT application WO2011064275A1, the two core elements may be placed in the overlapping arrangement by a certain mismatch in transport speed of the leading core versus the trailing core.

The secondary core may have different properties and functionalities as the first one.

For example, the primary core, as may be positioned at least in the rear portion of the article, may be designed such that urine is best handled when it contacts the wearer oriented surface, such as by having a wearer oriented surface executed with particular liquid acquisition properties, followed (away from the user) by a liquid distribution property region, and further a liquid storage functionality furthermost away from the user.

In a further particular execution, an article according to the present invention comprises a genital pocket. To this end, either a portion of the flexible faeces separation member located between the anus and the genitals during use is overfolded cross-directionally or a separate genital pocket material is attached to the flexible faeces separation member in this region, as will be described in more detail in the context of a particular embodiment. The genital pocket is sized to retain the genitals, i.e. the scrotum and/or penis for a male user, and the labia, especially in case of a pendulous labia, in case of a female user, away from faeces receiving regions, and/or prevent sagging of the genitals into faeces receiving parts of the article.

The articles according to the present invention may further comprise faeces guide means so as to ease the directional transport of faeces away from the loading point, i.e. the region positioned at the anus during use. Such faeces guide means may comprise surface property modifier, such as a surface friction reducer, a surface wettability reducer, a faeces adherence reducer, and/or surface structuring. Such a surface structuring may comprise at least one cross-directionally extending faeces strip, connected with its rearward oriented margin to the basis or said flexible faeces separation member and exhibiting a first faeces strip surface oriented to the surface, to which it is connected, whilst its forward oriented margin is essentially unconnected. In a preferred execution, the two opposite surfaces of the faeces strip exhibit different properties than the opposite surface, whereby the differences may be based on one or more of the following effects:

(a) for essentially same surface materials by roughening, or additive treatment, and/or by using an aperture film material forming "formed film", and/or (b) for different surface materials the use of rough vs. smooth materials, and/or non-absorbent versus absorbent materials.

A further particular execution builds on the good fit of an article of the present invention, which not only provides better retention of urine and faeces, but which provides almost gas tight sealing—or at least significantly improvements—at the legs and waist hoops. Henceforth, flatulus filter, such as well known from colostomy bags, but also as diaper implements, such as described in US2004/00010841A1, WO10/005603A1, or GB2296660A can be readily and effectively implemented. Within the present context, two executions thereof are preferred, both being based on the good adaptation of the product to the contours of a wearer. In a first execution, the outer layer of the article is essentially gas tight, but in the waist hoop region filter material may be introduced, such as in the form of a foamy material with filter material, such as charcoal. In a further execution, the outer layer is executed as a "breathable" material, as also well known in the art and odour absorbent material may be positioned over the full inward (or wearer oriented) surface.

In yet a further particular execution, an article according to the present invention comprises a skin/body adherence substance. Such substances are well known in the art, such as described in WO 00/00111 (Palumbo). The body adherence substance may be applied to the article in regions where the flexible faeces separation member can detach from the basis, and be executed such that it is covered by a removable cover, or such that its adherent surface is exposed upon opening the article.

Optionally, the substance may also develop its adhering properties during use, such as when employing a temperature triggered substance.

The present invention is now further explained by referring to particular executions, which however should not be seen as limiting the invention thereto.

In a first embodiment as depicted in FIG. 1 A to D, the flexible faeces separation member is executed as a faeces trap sheet 1030 which comprises discontinuity 1040, such as a slit or cut or an opening extending through its thickness. This discontinuity is intended to be positioned in registry with the anal opening of the wearer during use and it should allow faeces to pass through.

As shown in FIG. 1, the discontinuity intercepts the rear cross-directionally extending margin 1037 and will have a longitudinal extension of less than about 20 cm, preferably less than about 5 cm.

It is an essential feature of the present invention, that the wearer facing surface of the faeces trap sheet 1030 is attached to the longitudinal side margins of overfolded basis 1010 in the proximity of the discontinuity 1040 whilst its opposite surface is left disconnected to the underlying portion of the basis. This is shown in FIGS. 1B and C depicting an article 1000 with its basis 1010 folded over along longitudinal foldlines 1027 such that the longitudinal side margins 1023 are positioned towards the centre line 1004. Whilst the front (1013) and rear (1019) side panel regions may be backfolded again (as indicated in FIG. 1B by showing the topsheet surface 1022 in these regions and the backsheet surface 1028 in the crotch region), the basis is not backfolded at least in certain portions of the crotch region, as also indicated in FIG. 1C showing a cross-sectional view of the crotch region of an article. The faeces trap sheet 1030 with the discontinuity 1040 is attached at least with its lateral (1031) and its forward (1036) margin to the underlying basis 1010 but left essentially unattached apart from the pick-up connection 1045. This pick-up connection is positioned laterally outwardly of the discontinuity 1040 and connects at least parts of the perimeter of the discontinuity to areas in the vicinity of the longitudinal side margins 1023 of the basis. Thus, in the embodiment as shown in FIG. 1C, the faeces trap sheet 1030 is connected at its outer perimeter to this basis by connection 1032 whilst it is connected by the pick-up connecting 1045 with its opposite surface to the basis around the perimeter of the discontinuity. Preferably the crossdirectional distance between the pick-up connection and the perimeter of the discontinuity is less than 8 cm, more preferably less than 2 cm and may be zero. Similarly, the distance between the longitudinally extending side margins and the pick-up connection is preferably less than 8 cm, more preferably less than 2 cm, and may be zero. The spacing between the overfolded longitudinally extending side margins of the basis is preferably less than 10 cm, more preferably less than 5 cm, and may be zero, and correspondingly the distance of these side margins from the longitudinal centre line is half of it. Overlapping of the overfolded regions is less preferred, though it is contemplated to be within the scope of the present invention. Preferably, a backfolding of the basis material in the crotch region should be avoided. In another execution of this embodiment, the faeces trap sheet may cover the full surface of the article, and hence also cover all of the basis. In this case, the topsheet of the basis does not need to cover all its surface, and may, for example be executed as a strip material. This strip material may also have other and/or additional functionalities as a conventional topsheet, for example it may have particular liquid handling, i.e. acquisition or distribution properties. The surface trap sheet would then partly function as overall topsheet as well as faeces trap sheet provided the faeces storage area is not bonded to the layer below, it is slit and it holds pickup (e.g. glue) points left and right of the slit. In this embodiment the faeces trap sheet is preferably attached to the uppermost layer of the basis at least at the perimeter of the basis. It may additionally be attached more inwardly so as to prevent excessive distribution of the faecal material.

This has to be seen in contrast to "conventional" designs as well known in the art (see for example U.S. Pat. No. 3,426,756) as depicted in FIGS. 2 A and B. Therein, the basis 2010 of an article (2000) is folded into a Z-configuration (as can be seen in the left section of FIG. 2B and mirrored in the right section) along a first (2021) and a second (2022) fold line. The longitudinal side margins 2023 are extending laterally outwardly from the second fold line and this folding is affixed by a connection 2045, often referred to as centre glue. Even if such a design would be combined with a secondary topsheet in a conventional manner, it would not create the functionality of the present invention.

This is further explained when considering FIG. 1D showing (though not to scale) an article as depicted in FIG. 1A to C (where they are shown in a pre-use configuration) in its in-use configuration.

To this end the crotch or groin region of a wearer 1200 with legs 1212, buttocks 1214, gluteal groove 1220, and the anus 1230 is schematically depicted. The article 1000 is fitted between the legs, with its basis 1010 forming a "bucket" to which the faeces trap sheet 1030 is connected at the lateral perimeter along connecting lines 1032. Apart from this connecting, the faeces trap sheet may (in this cross-directional view corresponding to FIG. 1C) essentially only be connected further to the basis adjacent to the faeces passage, here shown as the discontinuity in the form of a slit 1040, by means of the pick-up connection 1045. Upon donning, the basis of the article will fit into the groin creases between the torso and the legs, thusly exerting cross-directional pull forces and thusly opening the faeces passage sufficiently to allow faeces passing through.

In a further execution of this embodiment the discontinuity corresponds to the rearward margin of the faeces trap sheet, which is extending close to the point corresponding to the positioning of the anus of a wearer during use, as indicated by the dash-dotted line 1037' in FIG. 1A. As described in the above, the faeces trap sheet is connected by pick-up connection 1045 to the overfolded part of basis 1010 in the proximity of the side margins 1023 thereof, such that preferably the cross-directional distance between the pick-up connection 1045 and the longitudinal centre line is less than 8 cm, more preferably less than 2 cm and may be zero. When the article is put into its in-use configuration, the pick-up connection lifts the faeces trap 1030 sheet away from basis 1010 thereby creating an opening for faeces to accumulate between the faeces trap sheet and the basis.

As indicated in the embodiment shown in FIG. 1A, the faeces trap sheet 1030 does not need to overly the total surface 1022 of the article. It should be positioned at least in the crotch region 1015 of the article extending backwardly at least towards the anus of the wearer during use. The size of the faeces trap sheet 1030 should be adapted to allow creation of a pocket sufficiently large to receive faeces or a bowel movement.

The width 1039 of the faeces trap sheet 1030 will be limited by the width of the basis in the crotch region. Of course, the absolute dimensions of the faeces trap sheet will depend on the size of the product and may be larger for adult incontinence products than for baby diapers. Typically, the faeces trap sheet will have a width of less than 100%, often less than 90% or 75% of the crotch width of the article. Preferably, it should not be narrower than the "crotch width" of a wearer, i.e. the left to right distance of the crotch groin, i.e. between the creases of the juncture of the torso and the legs. The faeces trap sheet is affixed at its longitudinally extending side margins 1031 and optionally at its forward cross directionally extending side margin 1036 along connecting lines or regions 1032 to the underlying layer, which is typically the primary topsheet of the basis, though it may extend outwardly over the connecting lines or regions 1032. This connecting is preferably executed such that solid or semi-solid exudates cannot pass through, and may be a glue line or an ultrasonic welding line as well known in the art. The connecting at its forward cross directionally extending side margin 1036 can be omitted such as to allow easy removal of faeces when undonning the article. This connecting may also be executed in a easy-to-open execution, such that during use the connecting holds and prevents forward distribution of the faeces, but upon undonning of the loaded article—possibly supported by some shaking of the article—this connecting opens and allows disposal of the faeces into a suitable disposal means such as a toilet. At its rear perimeter, the faeces trap sheet may be affixed along its margin 1037 to the underlying layer, or it may be left loose.

A skilled person will readily realize that the term "connecting line" includes areas extending in the x- and y-direction, such as a wide glue line, or a welding pattern. Also, whilst the faeces trap sheet is described in a rectangular embodiment, deviations from this shape are also within the scope of the present invention, such as when the faeces trap sheet is of an oval, elliptical, circular or even irregular shape, and a skilled person will readily adapt respective terms and features.

The article according to some executions of this embodiment includes a faeces passage which is adapted to allow faeces to be deposited between the faeces trap sheet and the first surface of the basis. In a pre-use configuration, the faeces trap sheet and the first surface of the basis may be in a contacting position without being completely attached to each other, such that they can be spaced apart. This spacing apart may be accomplished by the re-configuration of the article during use, and/or may be accomplished or furthered by the deposition of faecal material.

The faeces passage is delimited at least partially by a discontinuity of the faeces trap sheet. Within the present context, the term discontinuity refers to the result of a separating or severing action throughout the thickness of the faeces trap sheet, such as by cutting, which may have been applied to the faeces trap sheet prior to its application or thereafter by a variety of cutting or other devices of the types known to those skilled in the art.

In a first execution, this discontinuity may be a rectilinear or curvilinear cut in the faeces trap sheet, which may start and terminate within the material without intersecting a margin of the material. In another execution, the cut may intersect a margin of the faeces trap sheet, in particular the rearward margin thereof. In a further execution, the discontinuity may be a part of a margin.

The discontinuity will have a positioning and a longitudinal extension adapted to allow faeces to pass into the faeces trap. Thus, in an in-use configuration, the faeces passage, which comprises the discontinuity, will be positioned in the proximity of the anus of a wearer, and henceforth the discontinuity will typically be positioned around the longitudinal centreline of the article such that the discontinuity at least intersects the centreline. It may be positioned along this centreline such as when a straight cut is executed along the centre line. Optionally, this cut along the centreline may intersect the rear margin of the faeces trap sheet. Alternatively, the discontinuity may be a terminating margin of the faeces trap sheet, such as the rear cross-directionally extending margin thereof. The discontinuity will have a longitudinal extension (i.e. the projection of the discontinuity onto the longitudinal centreline) which should not be too large, as otherwise no separating effect between faeces and the skin of the wearer can be affected. Thus, the discontinuity should have a longitudinal extension of less than 20 cm, preferably less than 10 cm. The longitudinal extension may be less than this, e.g. when the discontinuity is executed as a longitudinally extending cut intersecting the rear margin of the faeces trap sheet, and it may actually be zero in the case of the discontinuity being the rearward cross-directionally extending margin itself Optionally, a further connecting of the faeces trap sheet and the underlying basis may be done in the proximity of the discontinuity such as the rear perimeter thereof and extend from the lateral outward folding towards the centre line, but preferably not more than about 50% of the distance between a pick-up connection on a side margin and the corresponding one on the faeces trap sheet.

Figure 5:
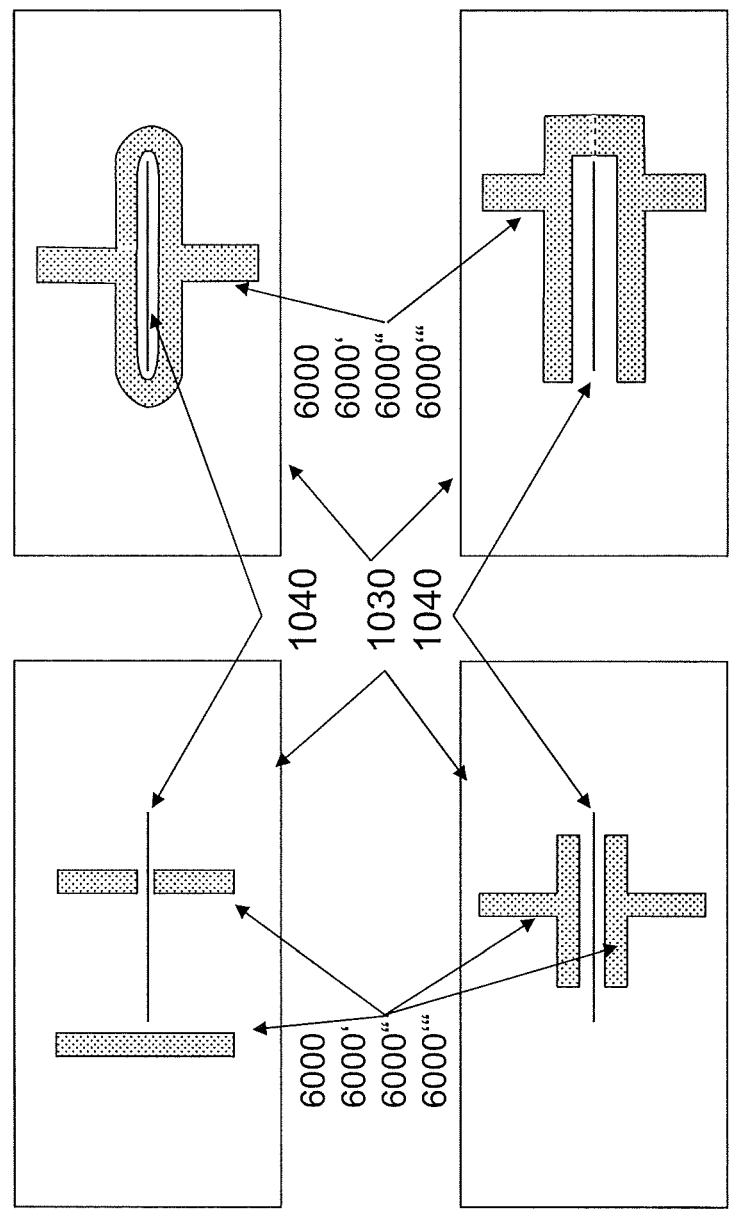
FIG. 5 shows schematically several executions of stiffening members according to one embodiment of the present invention.

FIG. 5 schematically depicts a preferred execution of this embodiment, wherein the faeces passage is created or maintained before or during use by means of a stiffening member 6000, which may have various shapes such as and which is connected to a faeces trap sheet 1030, here shown in a longer execution as compared to FIG. 1, and with a discontinuity, here indicated as a slit 1040, which is intended to be positioned in registry with the anus of a wearer during use.

For the formation of a genital pocket in this embodiment, the forward perimeter of the faeces trap sheet may be folded along a cross-directionally extending fold line before the longitudinal fold along line is executed. The overfolded portion is affixed on both sides at a distance of more than 1 mm, preferably more than 4 cm away from the longitudinal centreline to the overfolded side margins. Between these fixations, the now forwardly oriented margin of the overfolded portion of the faeces trap sheet is essentially unaffixed. During use, a genital pocket is shaped, into which the genitals, i.e. the scrotum and/or penis for a male user, and the labia, especially in case of a pendulous labia, in case of a female user are placed.

Further particular executions of the present embodiment relate to the ability of the faeces trap to readily receive faecal material without allowing them to flow back. To this end, that faeces trap as being formed by the outwardly oriented surface of the basis and the inwardly oriented surface of the faces trap sheet may be at least in portions equipped with faeces guide means, promoting the movement of faeces into the trap. In a first execution of this embodiment, the guide means comprise a surface property modifier, such as by employing surface friction reducer and/or surface wettability reducer, such as well known in the art. The surface property modification may comprise structuring the surface macroscopically, such as may be achieved by implementing one or more cross-directionally extending faeces strips, which are connected with their rearward oriented margin to said topsheet or said faeces trap sheet and exhibiting a first faeces strip surface oriented to the surface, to which it is connected, whilst its forward oriented margin is essentially unconnected. Preferably, the first faeces strips surfaces exhibit different friction properties than the opposite surface. This difference in properties can be achieved by using one layer of material or several layers of material with essentially the same type of material being on the surfaces, but the different properties of the surfaces are achieved by treating the surfaces differently, such as by roughening or additive treatment. The one or multi-layer material may also have a macrostructure with directional flow or surface properties, such as may be achieved by macroscopically expanded formed films, such as described in more detail in U.S. Pat. No. 4,601,868, or slanted capillary member as described in EP1040800A2. Alternatively, two different materials may form the first and opposite surfaces of the faeces strips with properties as described, i.e. the first surface may be smooth, and the opposite may be rough, or made of a formed film or slanted capillary material. The opposite surface may also be formed of a particular faeces handling or—such as for low or medium viscosity faeces—faeces absorbing material, such as described in WO01/06974.

Yet a further execution of the present invention relates to a faeces trap sheet, which exhibits liquid absorbency properties and may be in capillary liquid communication with the main core. Such "secondary cores" are well known in the art, such as generally described in JP08196565A2, or EP1234563A1, or in WO06/108029A1 in the context of removable cores.

Exemplary materials and structures that may be utilized in the absorbent core structure of the present invention are for example described in U.S. Pat. No. 5,531,728 (Lash), U.S. Pat. No. 5,147,345 (Young), U.S. Pat. No. 5,800,416 (Seger), U.S. Pat. No. 6,372,953 (Young), U.S. Pat. No. 5,260,345 (DesMarais). The absorbent core components may also include a combination of various absorbent materials, for example, a combination of foam and wood pulp or other cellulosic fibres and/or particles or fibres of a polymeric absorbent gelling material. Suitable absorbent structures may exhibit an absorbent capacity of 2 g/g, preferably more than 4 g/g, or even more than 10 g/g, such as when evaluated by the teabag centrifuge capacity, as described in more detail in U.S. Pat. No. 5,714,156.

In a second embodiment of the present invention the flexible faeces separation member is executed by adapting the topsheet of the basis in a particular manner, namely by including one or more cross-directional z-folds therein, whereby the wearer oriented part of the z-fold is essentially unattached to the basis but attached by the pickup connection.

In a first execution of this embodiment, as depicted in FIG. 4A, a cross-directional z-fold in the topsheet 4000 is positioned during use forwardly of the anus. In the variant of this execution as depicted in FIG. 4A, the base of the z-fold 4050, which is oriented towards the basis of the article or the preform there for and which is shown with an absorbent core 4010 and a backsheet 4020, may be connected thereto. The upper basis of the z-fold, which is oriented towards the wearer is connected to side margins of the centre piece at least in the proximity of the pick-up connection by a connection 4060. The base of the z-fold is attached to the basis at least in the proximity of the side margins of the basis. The execution as shown in FIG. 4A has a cross-bar of the z-fold running forwardly, and thus a genital pocket may be formed.

FIG. 4B depicts a further variant of this execution, wherein also a z-fold 4070 is incorporated into the topsheet of the basis. However, in this execution the cross-bar of the z-fold is running backwardly, such that a faeces movement barrier is created similar to the faeces trap as described in the above.

A further execution of this embodiment comprises a further z-fold 4080, now positioned rearwardly of the anus during use. Also in this execution, the basis oriented base of the z-fold is attached thereto basis and the wearer oriented base of the z-fold is connected to the overfolded side portions of the basis. As shown in FIG. 4C, the cross-bar of the z-fold in this execution is oriented forwardly. This execution is preferably combined with either or both executions of the forwardly positioned z-fold as shown in FIG. 4E.

Optionally, the topsheet comprises the discontinuities, such as apertures to allow faeces to pass through. These apertures may be positioned in the cross-bars of the z-folds 4070 and/or 4080.

Optionally, the topsheet may further comprise faeces guide means as described in more detail for the embodiment with a faeces trap sheet.

It should be noted that none of the described embodiments should be seen to limit the present invention. Also, a skilled person will readily realize that the various embodiments can be combined with other ones.

The invention claimed is:

1. An article for being worn on a lower torso of a wearer, said article comprising:
   a basis formed of a liquid impervious back sheet and an absorbent core, said basis having a front region, a rear region and a crotch region there between, thereby defining a longitudinal (x-) and width (y-) direction, a longitudinal centre line and two opposite longitudinally extending side margins having an outer edge, said basis exhibiting a first surface defined on the absorbent core and intended to be oriented towards a wearer during use; and a second surface defined on the back sheet and intended to be oriented away from the wearer during use; and a flexible faeces separation member attached to said first surface of said basis, whereby the attachment is adapted to allow spacing apart of said flexible faeces separation member from said first surface of said basis at least along a portion of said longitudinal centre line, wherein;

said longitudinal side margins of said basis are overfolded such that its first surface overlays said flexible faeces separation member at least in the crotch region;

and said first surface of said overfolded longitudinal side margins is connected to said flexible faeces separation member by a pick-up connection, which;

(i) is located at a distance of less than 2.5 centimeters from the outer edge of the overfolded longitudinal side margins, and (ii) is positioned longitudinally at least in the crotch region of the article, wherein said flexible faeces separation member is a faeces trap sheet that overlies said first surface at least in the crotch region and forms a faeces trap between said faeces trap sheet and said first surface;

said flexible faeces separation member remains essentially unattached to said absorbent core in the proximity of the pick-up connection; and said faeces trap further comprising a faeces passage delimited at least partially by a discontinuity of said faeces trap sheet, said passage being adapted to allow faeces to be deposited between said faeces trap sheet and said first surface, and said passage being positioned along or intersecting said longitudinal centre line.

2. An article according to claim 1, wherein said pick-up connection
(iii) has a longitudinal extension of less than 30 cm.

3. An article according to claim 2, wherein said pick-up connection has a longitudinal extension of less than 15 cm.

4. An article according to claim 2, wherein said pick-up connection has a longitudinal extension of less than 5 cm.

5. An article according to claim 1, further comprising a stiffening element attached to said flexible faeces separation member in the crotch region and to a leg hoop or said pick-up connection.

6. An article according to claim 5, wherein said stiffening element comprises a cross-directionally extending strip of material, having a stiffness higher than the stiffness of said flexible faeces separation member.

7. An article according to claim 1, wherein said flexible faeces separation member is adapted to form a genital pocket.

8. An article according to claim 1, wherein said flexible faeces separation member comprises faeces guide means for directional faeces transport, comprising a surface property modifier selected from the group consisting of:
a surface friction reducer,
a surface wettability reducer,
a faeces adherence reducer, and
a surface structuring.

9. An article according to claim 1, further comprising a flatulus filter material.

10. An article according to claim 9, wherein said flatulus filter material is positioned in a waist hoop region of said article or between a topsheet and the second opposite surface of said basis.

11. An article according to claim 1, further comprising a body adhering substance.

12. An article according to claim 1, wherein said discontinuity is a slit extending through the faeces trap sheet.

13. An article according to claim 12, wherein said discontinuity is a slit extending essentially longitudinally.

14. An article according to claim 13, wherein said slit extends at a length of at least 1 cm.

15. An article according to claim 13, wherein said slit extends at a length of less than 90% of the length of the faeces trap sheet.

16. An article according to claim 1, further comprising absorbent material connected to or integral with said faeces trap sheet such that said absorbent material exhibits a teabag centrifuge absorbent capacity of at least 2 g/g, said absorbent material being essentially unattached to said basis at least along the longitudinal centre line at least in a portion of the crotch region.

17. An article according to claim 1, wherein said pick-up connection is positioned cross-directionally relative to said longitudinal centre line at a distance of less than 5 cm.

18. An article according to claim 1, wherein said pick-up connection is positioned cross-directionally relative to said longitudinal centre line at a distance of less than 2.5 cm.

19. An article according to claim 1, wherein said discontinuity intersects a margin of said faeces trap sheet.

* * * * *